US00PP18229P2

(12) United States Plant Patent
Ishihara et al.

(10) Patent No.: US PP18,229 P2
(45) Date of Patent: Nov. 20, 2007

(54) ***PETUNIA* PLANT NAMED 'SUNSURFCOPASAMO'**

(50) Latin Name: *Petunia hybrida Vilm.*
Varietal Denomination: Sunsurfcopasamo

(75) Inventors: Takuro Ishihara, Tokyo (JP); Kazunari Iwaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/443,650

(22) Filed: May 31, 2006

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *petunia* plant particularly distinguished by medium-size, single, pink flowers with red-purple venation, abundant branching with a great profusion of blooms, excellent tolerance to low temperatures, and a compact, mounding growth habit is disclosed.

2 Drawing Sheets

Genus and species: *Petunia hybrida* Vilm.
Variety denomination: 'Sunsurfcopasamo'.

BACKGROUND OF THE NEW PLANT

The present invention comprises a new and distinct cultivar of *petunia,* botanically known as *Petunia hybrida* Vilm., and hereinafter referred to by the cultivar name 'Sunsurfcopasamo'. The new cultivar originated from a hybridization made in May 2002 in Higashiomi, Shiga, Japan. The female parent was a cultivar *petunia* plant 'Fantasy Crystal Red' (unpatented), while the male parent was a proprietary *petunia* plant 'P01-583' (unpatented).

The new cultivar was created in 2002 in Higashiomi, Shiga, Japan and has been asexually reproduced repeatedly by vegetative cuttings in Higashiomi, Shiga, Japan. The present invention has been found to retain its distinctive characteristics through successive asexual propagations.

SUMMARY OF THE INVENTION

The following are the most outstanding and distinguishing characteristics of this new cultivar when grown under normal horticultural practices in Higashiomi, Shiga, Japan.

A) Single, medium-size, pink flowers with red-purple venation;

B) Abundant branching with a great profusion of blooms;

C) Compact and mounding plant habit;

D) Whole plant remains in bloom for a considerable period of time; and

E) Excellent tolerance to low temperatures.

DESCRIPTION OF PHOTOGRAPHS

This new *petunia* plant is illustrated by the accompanying photographs which show blooms and foliage of the plant in full color, the colors shown being as true as can be reasonably obtained by conventional photographic procedures. The photographs are of a 4-month-old plant grown in a greenhouse in Higashiomi, Shiga, Japan.

DESCRIPTION OF THE NEW CULTIVAR

Figure 1:
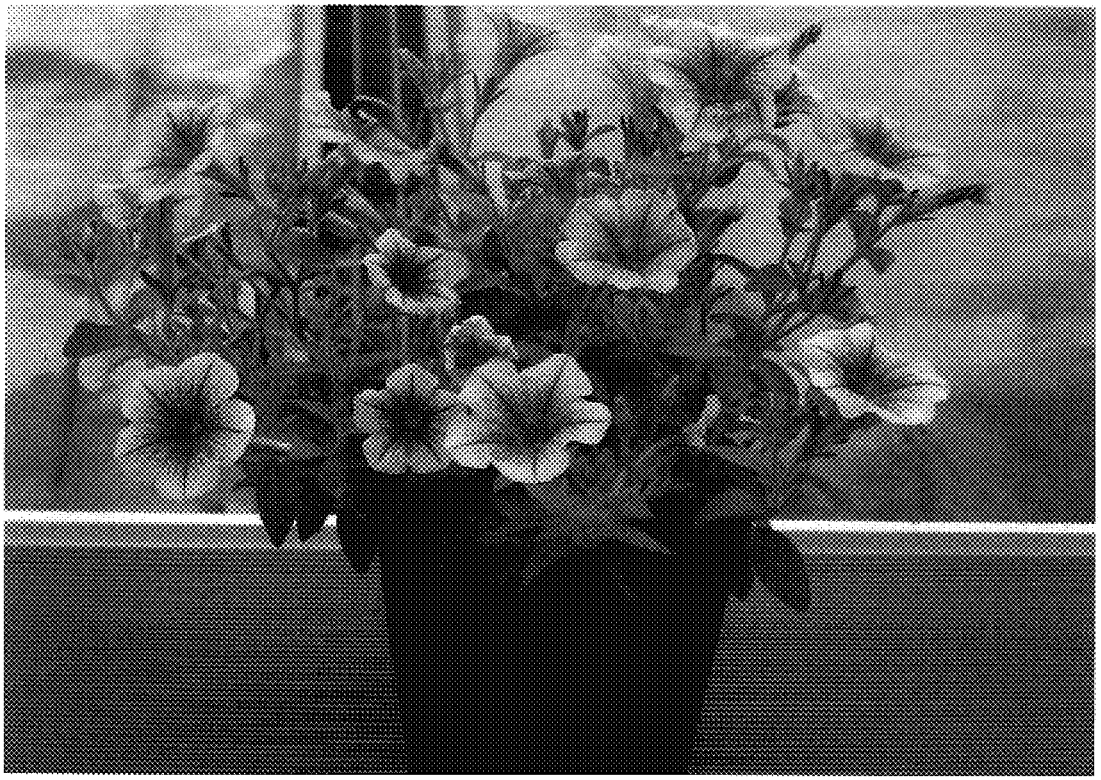
FIG. 1 shows the overall plant habit, including blooms, buds and foliage.
Figure 2:
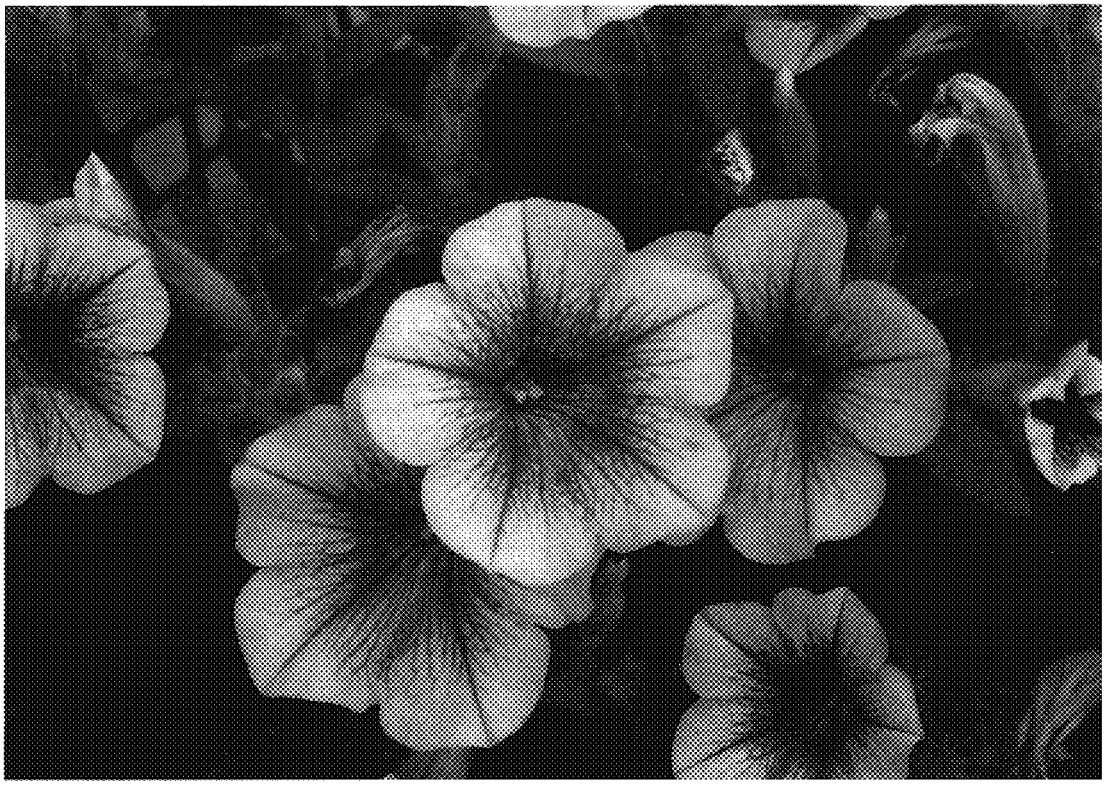
FIG. 2 shows mature flowers.

The following detailed description sets forth the distinctive characteristics of 'Sunsurfcopasamo'. The data which define these characteristics were collected from asexual reproductions carried out in Higashiomi, Shiga, Japan. The plant history was taken on 4-month old plants which were planted as rooted cuttings in 15-cm pots in 2005 and grown in a greenhouse between 13° C. and 23° C. The plants were pinched once in April 2005. Observations were made when the plants were in full flower in June 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Solanaceae.
- *Botanical.*—*Petunia hybrida* Vilm.
- *Common name.*—*Petunia.*

Parentage:
- *Female parent.*—'Fantasy Crystal Red', a cultivar bright-red (RHS 52A) with light rose-red venation flowered *petunia* plant (unpatented).
- *Male parent.*—'P01-583', a proprietary pink with red-purple venation flowered *petunia* plant (unpatented).

Growth:
- *Form.*—Annual.
- *Habit.*—Compact and mounding, freely branching, vigorous.
- *Height* (*measured from the top of the soil*).—15.2 cm.
- *Diameter or area of spread.*—34.6 cm.
- *Propagation.*—Terminal tips for cutting.
- *Time to produce a finished flowering plant.*—About 2 to 3 weeks, in April to late October, for a 15-cm pot.
- *Keeping quality.*—210 days.
- *Outdoor plant performance.*—Use in containers, pots and landscaping; excellent tolerance to temperatures below 5° C.
- *Time to initiate and develop roots.*—7 days at 20° C. to 25° C.
- *Time to produce rooted cutting or liner* (*young plant*).—21 days at 20° C. to 25° C.

*Root description.*—Light brown, fibrous, fine; fleshy, freely-branching.

Branches:

*Number of branches.*—6 basal branches; 18 lateral branches.

*Length of lateral branches.*—13.6 cm.

*Diameter of lateral branches.*—0.21 cm.

Stems:

*Description.*—Round in cross-section.

*Color.*—RHS 144A.

*Stem length.*—13.6 cm.

*Diameter.*—0.21 cm.

*Internode length.*—1.9 cm.

*Anthocyanin.*—Absent.

*Texture.*—Pubescent.

Leaves:

*Arrangement.*—Alternate, single leaves, 12.8 leaves per lateral branch.

*Apex.*—Acute.

*Base.*—Rounded.

*Color (mature leaves).*—Upper surface: RHS 137B. Lower surface: RHS 146C.

*Color (immature leaves).*—Upper surface: RHS 137B. Lower surface: RHS 146C.

*Margin.*—Entire.

*Size.*—Length: 4.7 cm. Width: 2.2 cm.

*Shape.*—Ovate.

*Texture.*—Pubescent both sides.

*Venation.*—Type: Reticulate. Color: Upper surface: RHS 144C. Lower surface: RHS 144C.

*Petiole.*—Length: 0.75 cm. Diameter: 0.14 cm. Color: RHS 144C. Texture: Pubescent.

Flower buds:

*Color.*—RHS N144D.

*Shape.*—Cylindrical.

*Size.*—Length: 3.7 cm. Diameter: 0.47 cm.

Inflorescence:

*Blooming habit.*—Continuous from Spring to Fall.

*Inflorescence type.*—Single flower, self-cleaning.

*Arrangement.*—Borne in upper leaf axils.

*Aspect.*—Upright to outward.

*Shape.*—Single, salverform.

*Fragrance.*—Absent.

*Flower number (per inflorescence).*—One.

*Quantity of flowers and buds per plant.*—91.

*Flower longevity on plant.*—5 days.

*Peduncle.*—Color: RHS 144A. Length: 3.1 cm. Diameter: 0.11 cm. Texture: Pubescent, viscid. Angle: Outward.

Flowers:

*Size.*—Height (flower depth): 3.6 cm. Diameter: 5.1 cm.

*Corolla tube.*—Shape: Tube. Length: 2.8 cm. Diameter (proximal end): 0.28 cm. Color (outside): RHS N77D with RHS N144D venation. Texture: Pubescent.

*Petals.*—Arrangement: Single whorl. Shape: Very broadly obovate, fused. Quantity: 5. Size: Length (from the throat): 2.0 cm. Width: 2.4 cm. Apex: Rounded. Base: Fused. Margin: Entire, weakly undulated. Color (when opening): Upper surface: RHS 73B with RHS 60B venation. Lower surface: RHS 75C with RHS 54A venation. Color (fully opened): Upper surface: RHS 75B with RHS 60B venation. Lower surface: RHS 75C with RHS 54A venation. Throat color (inside): RHS 150C with RHS 176B venation. Throat diameter (distal end): 0.94 cm. Petal texture (both surfaces): Smooth, satiny.

*Calyx.*—Form: Tubular, star-shape. Length: 1.3 cm. Diameter: 1.4 cm.

*Sepals.*—Arrangement: Single whorl. Number: 5. Shape: Elliptic. Apex: Rounded. Base: Fused. Margin: Entire. Size: Length: 1.02 cm. Width: 0.25 cm. Color (mature): Upper surface: RHS 137A. Lower surface: RHS 137C. Color (immature): Upper surface: RHS 137A. Lower surface: RHS 137C.

Reproductive organs:

*Stamens.*—Quantity: 5. Filament: Length: 1.5 cm to 2.0 cm. Color: RHS 145C. Anther: Shape: Ellipsoidal. Size: Length: 0.2 cm. Width: 0.2 cm. Color: RHS 10D.

*Pollen.*—Amount: Moderate. Color: RHS 10B.

*Pistil.*—Quantity: One. Length: 1.84 cm.

*Style.*—Length: 1.7 cm. Color: RHS 144D.

*Stigma.*—Shape: Transversely ellipsoidal. Color: RHS 143B.

*Ovary color.*—RHS 144A.

Fruit and seed set: Seed production has not been observed.

Disease and insect resistance: No particular resistance or susceptibility to diseases or insects noted to date.

COMPARISON WITH PARENTAL AND COMMERCIAL CULTIVARS

'Sunsurfcopasamo' differs from the female parent 'Fantasy Crystal Red' (unpatented), by having pink flowers with red-purple venation, while 'Fantasy Crystal Red' has bright-red flowers with light rose-red venation. Additionally, 'Sunsurfcopasamo' has a mounding plant habit, while 'Fantasy Crystal Red' has an upright plant habit.

'Sunsurfcopasamo' differs from the male parent 'P01-583' (unpatented), by having a mounding plant habit and a larger flower diameter, while 'P01-583' has a decumbent plant habit and smaller flower diameter.

'Sunsurfcopasamo' is similar to the commercial variety 'Suncopablue' (U.S. Plant Pat. No. 16,355) however, there are differences as listed in Table 1 below:

TABLE 1

Comparison of Characteristics between 'Sunsurfcopasamo' and 'Suncopablue'

| Characteristic | 'Sunsurfcopasamo' | 'Suncopablue' |
|---|---|---|
| Growth Habit | Mounding | Decumbent |
| Leaf Shape | Ovate | Elliptic |
| Leaf Apex | Acute | Acute |
| Leaf length | 4.7 cm | 3.2 cm |
| Leaf color (mature) | Upper surface: RHS 137B Lower surface: RHS 146C | Upper surface: RHS 144B Lower surface: RHS 146C |
| Flower diameter | 5.1 cm | 4.4 cm |
| Flower height | 3.6 cm | 3.0 cm |
| Petal color (fully opened) | Upper surface: RHS 75B with RHS 60B venation Lower surface: RHS 75C with RHS 54A venation | Upper surface: RHS N87A Lower surface: RHS N87C |
| Throat color (inside) | RHS 150C with RHS 176B venation | RHS N81C |
| Corolla tube color (outside) | RHS N77D with RHS N144D venation | RHS 83B |
| Calyx length | 1.3 cm | 1.0 cm |
| Peduncle length | 3.1 cm | 1.8 cm |
| Anther color | RHS 10D | RHS 150D |
| Stigma color | RHS 143B | RHS 15C |

We claim:

1. A new and distinct cultivar of *petunia* plant as shown and described herein.

* * * * *